United States Patent [19]

Potter

[11] Patent Number: 5,268,301

[45] Date of Patent: Dec. 7, 1993

[54] METHOD FOR FILTRATION ASSAYING OF ISOTOPE-LABELLED PARTICULATE SAMPLES

[76] Inventor: Colin G. Potter, 12 Beech Road, Headington, Oxford, United Kingdom

[21] Appl. No.: 697,313

[22] Filed: May 8, 1991

[51] Int. Cl.$^5$ .................. G01N 21/77; G01T 1/20
[52] U.S. Cl. .................... 436/57; 436/166; 436/177; 436/178; 436/542; 436/804; 250/362; 250/364
[58] Field of Search .............. 436/57, 58, 524, 528, 436/542, 166, 169, 177, 178, 804; 250/361 R, 364, 362

[56] References Cited

U.S. PATENT DOCUMENTS

| | | | |
|---|---|---|---|
| 4,271,139 | 6/1981 | Hart | 436/523 X |
| 4,298,796 | 11/1981 | Warner et al. | 250/328 |
| 4,451,434 | 5/1984 | Hart | 436/523 X |
| 4,562,158 | 12/1985 | Schellenberg | 436/57 |
| 4,728,792 | 3/1988 | Warner et al. | 250/328 |
| 4,916,320 | 4/1990 | Wunderly et al. | 250/364 X |

*Primary Examiner*—James C. Housel
*Assistant Examiner*—Jeffrey R. Snay
*Attorney, Agent, or Firm*—Willian Brinks Olds Hofer Gilson & Lione

[57] ABSTRACT

A method for filtration assaying a particulate sample labelled with low-energy radioactive isotopes measurable by scintillation counting. The method aspect of the invention includes the step of providing a sample comprising sample particles labelled with low-energy radioactive isotopes in a liquid medium. Scintillant particles are added to the liquid medium. The sample is then filtered with a filter medium adapted to retain the sample particles and the particles of scintillant, such that after filtration the sample particles are each surrounded by scintillant. A photodetector is then used to detect light emitted by the scintillant on the filter medium.

31 Claims, No Drawings

METHOD FOR FILTRATION ASSAYING OF ISOTOPE-LABELLED PARTICULATE SAMPLES

BACKGROUND OF THE INVENTION

The present invention relates to methods and compositions used in filtration assaying of isotope-labelled particulate sample.

Many biological, and other, samples containing radioactive isotopes are counted by liquid scintillation counting. Samples may be dissolved in scintillant or, if insoluble and finely divided, may be suspended in scintillant gels. Particulate samples may also be filtered onto a filter support layer and this is often used where unincorporated isotope must be washed from the sample, for example from biological cells.

Semi-automated harvesting methods exist for this procedure but the samples must then be placed in liquid scintillant, usually in separate vials, before counting in a liquid scintillation counter. Recently, a new type of flat-bed scintillation counter has been developed whereby multiple samples deposited on a filter support are placed together in scintillant without being separated (See UK patent 1,586,966, U.S. Pat. No. 4,298,796). This allows a considerable reduction in preparation time and also in the amount of scintillant required. The scintillant however usually contains an organic solvent which poses problems of disposal even in small amounts. It is also a problem for some samples with small molecules which may dissolve in the liquid scintillant and thereafter diffuse away from the correct sample area thereby limiting the general use of the flat-bed scintillation counter.

There have been several attempts to solve these problems. One is to use a special sheet of solid scintillant which is heated until it melts and soaks into the filter. When the composite cools the scintillant solidifies and any further potential diffusion of the sample is halted.

As another solution, the filter itself may be composed of scintillant so that the close approximation of the sample particles to the filter gives rise to countable scintillations (UK patent 1,586,966, U.S. Pat. No. 4,298,796). A variant technique is that the filter may support solid scintillant particles (such as Yttrium silicate) on its surface, placed there by filtration, scattering or spraying onto appropriate adhesion means (Int. patent WO 89/02088), ready to receive the samples by filtration. However, for this and the previous method, about half the electrons emitted by the decaying atoms of isotope will pass straight out of the filter and therefore will not encounter the scintillant, with the result that the efficiency is thereby limited to a maximum of about 50%.

An improvement on this technique (Swedish patent 9901879-1, Int. patent PCT/GB89/00542) is to coat the fibers of the filter with a meltable scintillant such that, after filtration and drying, the filter may be heated so that the scintillant flows around the particles of sample and the counting efficiency is thereby considerably increased. Since the flow is on a microscopic scale there is no significant diffusion of soluble sample components away from the sample area. In practice, the solid meltable scintillant, the Yttrium silicate-filters and the meltable scintillant-coated filter all typically have a similar maximum counting efficiency of 70-80% compared with the best liquid scintillant methods.

SUMMARY OF THE INVENTION

Briefly stated, the present invention is a method and composition for filtration assaying a particulate sample labelled with low-energy radioactive isotopes measurable by scintillation counting. The method aspect of the invention includes the step of providing a sample comprising sample particles labelled with low-energy radioactive isotopes in a liquid medium. Scintillant particles are added to the liquid medium. The sample is then filtered with a filter medium adapted to retain the sample particles and the particles of scintillant, such that after filtration the sample particles are each surrounded by scintillant. A photodetector is then used to detect light emitted by the scintillant on the filter medium.

In accordance with the composition aspect of the invention, a composition is provided, preferably in the form of a compressed pellet, for use in filtration assaying a particulate sample liquid medium, said sample labelled with low-energy radioactive isotopes measurable by scintillation counting. This pellet includes scintillant particles capable of being retained on a filter medium held together by a binder material which releases the scintillant particles in the liquid medium.

In accordance with a preferred method of the present invention, the scintillant particles are provided in the form of a pellet. Preferably, the pellet also includes some meltable particles and the scintillant particles and sample particles are heated and compacted to thereby bind the two for ease of handling and improved light transmission during the detection step. Also in this preferred embodiment, the pellet further includes a compound which is capable of stopping the incorporation of the radioactive isotope by the sample.

As used in the specification and appended claims, the term "pellet" is intended to have a broad meaning, referring to a mass of the necessary ingredients formed into the appropriate shape and size for use in the filtration assaying method.

DETAILED DESCRIPTION OF THE PREFERRED EMBODIMENTS

In accordance with the present invention, yet another solution to the problems discussed above is presented. In particular, the scintillant, in the form of small particles or beads such as Yttrium silicate, is aliquotted as a slurry or a pellet into a vessel which holds the sample plus any unincorporated isotope in a liquid medium. Sample and scintillant are then filtered together onto any suitable retaining filter medium in such a way that virtually each sample particle is surrounded on all sides and packed in by solid scintillant. Unincorporated isotope will pass through the filter as usual. Preferably, the sample particles are washed to remove any residual unincorporated isotope. After drying, the counting efficiency of this filter is considerably increased compared with the technique having solid scintillant already in place on the surface of the filter.

The scintillant particles can be provided in many forms. Preferably, the scintillant particles comprise beads made from a material selected from the group consisting of yttrium silicate, yttrium aluminate, diphenyloxazole dissolved in a polymeric material, cerium doped lithium glass, europium activated calcium fluoride, as well as combination of these. Most preferably, the scintillant particles comprise beads of yttrium silicate. Alternatively, the scintillant particle comprise beads made from diphenyloxazole dissolved in polyvinyltoluene.

The amount of scintillant particles added will depend on several factors such as the size of the sample and the concentration of the sample particles in the liquid medium. Also, the size of the scintillant particles will effect the number of particles that are needed to surround the sample particles on the filter medium. Because the object is to surround the sample particles, the scintillant particles will preferably vastly outnumber the sample particles. It is considered to be within the skill in the art to select the appropriate number of scintillant particles depending on these factors.

Likewise, the size of the scintillant particles will depend on several factors such as the size of the sample particles and the nature of the filter medium. It is considered to be within the skill in the art to select the appropriate size of the scintillant particles.

Because particles composed of scintillants such as yttrium silicate are at present intrinsically more efficient at detecting low-energy electrons compared with the liquid or the meltable solid scintillants, it is possible to obtain slightly higher counting efficiency for this technique than using the best liquid scintillants.

The poor energy transfer between the sample and scintillant particles may reduce counting efficiency to a lower level than that theoretically possible. This is demonstrated in the examples below where a further increase in counting efficiency occurs upon the addition of liquid scintillant to such a filter.

In view of the above, in the preferred embodiment, the counting efficiency is improved by adding to the scintillant particles, meltable particles, e.g., a small amount of particulate meltable solid solvent, which may itself be or contain a scintillant. When the meltable particles are included, the sample is preferably heated, and most preferably heated and compacted to thereby bind the sample particles and scintillant particles together. The particles can be melted by, for example, heated rollers, a hot plate or a microwave oven.

This thermal binding step has been found to increase counting efficiency by improving the light output by improved optical coupling through the fused particles. This binding step also serves to bind the particulate scintillant and sample together on the filter to prevent accidental movement of scintillant and sample.

Preferably, the meltable particles will aid in the transmission of light from the scintillant particles to the photodetector means following compaction of the composite sample. Most preferably, these particles are made of a material selected from the group consisting of diisophenyl naphthalene and tetramethylmethylbenzine, as well as combinations thereof.

It is useful for some applications to include in the binder component, a substance that could stop the incorporation of isotope at the time of its addition. For example, for cells incorporating $^3$H-thymidine into their DNA in a proliferation assay, the incorporation will be greatly reduced if non-radioactive thymidine is added in considerable excess of the $^3$H-thymidine. Preferably, 100 $\mu$g thymidine per well is added. Alternatively, a detergent may be added to lyse the outer membrane of the sample cells. Likewise, metabolic inhibitors can be added which would also stop the incorporation of the radioactive isotope by the samples.

Preferably, the composition with the scintillant particles is formed into a pellet. Although the pellet may in some cases be self-binding, it will typically be held together with a binder material. Naturally, the binder should be inert enough not to affect the assay being used. Also, the binder may be selected from substances already present as a component of the sample. One example of such a binder is glucose, which is present in the growth media containing cells that may be incorporating labelled compounds. If the extra material would interfere with the assay, even if added just before harvesting, then anomers such as L-glucose could be used.

In alternative embodiments, the composition with the scintillant particles can be provided in the form of a powder or a slurry.

EXAMPLES

The following examples are provided by way of explanation and illustration. As such, these examples are not to be seen as limiting the scope of the present invention defined by the appended claims.

Filtration assays were set up for cells of two types. One was set up for the uptake of $^3$H-thymidine into a human leukemic cell line (K562) and the other for the much smaller cells of the malarial parasite plasmodium falciparum, labelled with $^3$H-hypoxanthine. Cells were set up in the appropriate medium, labelled overnight in microtitration plates and 50 $\mu$l aliquots of a slurry of $Y_2SiO_5$ in phosphate buffer added to each well of the microtitration plate. The plates were shaken briefly before harvesting 12 at a time onto glass fibre filters using a Skaatron cell harvester. These were counted using a flat-bed liquid scintillation counter and compared with controls that had been harvested without the addition of scintillant beads but with an efficient liquid scintillant added to the filtration sheet. After counting, liquid scintillant was added to the Yttrium silicate loaded sample sheet which was recounted. It was found that counting efficiency depended on the quantity of scintillant bead added. For these experiments 5 mg/well of Yttrium silicate was used.

| | Results | | | % of |
|---|---|---|---|---|
| | cpm | s.d. | C.V. | G/F |
| K562 cells - (n = 12) | | | | |
| Experiment a. | | | | |
| Glass fibre + liquid scintillant | 662.0K | 18.6K | (2.8%) | 100.0 |
| Y2SiO5 beads | 703.2K | 34.4K | (4.9%) | 89.0 |
| Y2SiO5 + liquid scintillant | 954.8K | 59.5K | (6.2%) | 144.2 |
| Experiment b. | | | | |
| Glass fibre + liquid scintillant | 753.7K | 18.9K | (2.5%) | 100.0 |
| Y2SiO5 | 798.3K | 31.0K | (3.9%) | 105.9 |
| Y2SiO5 + compaction by by heated rollers | 853.0K | 32.3K | (3.8%) | 113.2 |
| Malarial parasites - (N + 12) | | | | |
| Glass fibre + liquid scintillant | 19.28K | 0.42K | (2.19%) | 100.0 |
| Y2SiO5 | 17.64K | 1.37K | (7.78%) | 91.5 |
| Y2SiO5 + liquid scintillant | 29.96K | 1.05K | (3.51%) | 155.4 |

It is thus seen that an improved method for filtration assaying of particulate samples labelled with radioactive isotopes has been shown. Improvements in the counting efficiency are achieved by the use of the scintillant particles co-filtered with the sample particles. In addition, the preferred embodiment, wherein meltable particles are included and heat and compaction are used, achieves even greater efficiency.

It should be borne in mind that, although specific preferred and alternative embodiments have been disclosed, the scope of the invention is not limited to the details of these embodiments. Rather, it is the appended claims that define the scope of the present invention.

I claim:

1. A method for filtration assaying a particulate sample labelled with low-energy radioactive isotopes measurable by scintillation counting, the method comprising the steps of:
   providing a sample comprising sample particles labelled with low-energy radioactive isotopes in a liquid medium;
   adding to the liquid medium scintillant particles;
   simultaneously filtering the sample particles and scintillant particles in the liquid medium with a filter medium adapted to retain the sample particles and the particles of scintillant, such that after filtration the sample particles are each surrounded by scintillant; and
   using a photodetector to detect the degree of scintillation of the sample on the filter medium.

2. The method of claim 1 further comprising the step of washing the sample particles on the filer medium to remove unincorporated isotope.

3. The method of claim 1 wherein the scintillant particles comprise beads made from a material selected from the group consisting of yttrium silicate, yttrium aluminate, diphenyloxazole dissolved in a polymeric material, cerium doped lithium glass, europium activated calcium fluoride, as well as combination of these.

4. The method of claim 1 wherein the scintillant particles comprise beads made from diphenyloxazole dissolved in polyvinyltoluene.

5. The method of claim 1 further comprising the step of adding a compound that stops incorporation of isotope-labelled substances in an assay with the particles of scintillant, so as to prevent further incorporation of isotope in the sample.

6. The method of claim 5 wherein the radioactive isotope is $^3$H-thymidine, and thymidine is the compound that stops incorporation.

7. The method of claim 5 wherein the compound for stopping incorporation is a detergent for lysis of cell membranes.

8. The method of claim 5 wherein the compound for stopping incorporation is a metabolic inhibitor.

9. The method of claim 1 further comprising the step of compacting the sample particles and scintillant particles before using the photodetector.

10. The method of claim 9 further comprising the step of adding particles which aid in the transmission of light from the scintillant particles to the photodetector means following compaction of the composite sample.

11. The method of claim 10 wherein the particles which aid in the transmission of light are made of a material selected from the group consisting of di-isophenyl naphthalene and tetramethylmethylbenzine, as well as combinations thereof.

12. The method of claim 1 wherein at least some of the scintillant particles are meltable and comprising the further step of heating the sample particles and scintillant particles after filtration to thereby bind the scintillant particles and sample particles together.

13. The method of claim 12 further comprising the step of compacting the sample particles and scintillant particle while heating.

14. The method of claim 1 wherein the scintillant particles are compressed together in a pellet for ease of administration, such that the scintillant particles are dispersed after addition to the sample in the liquid medium.

15. The method of claim 14 wherein the pellet has an inert binder which will dissolve in the liquid medium and release the scintillant particles.

16. The method of claim 15 wherein the binder comprises a sugar which will not disturb the metabolism of a biological sample.

17. The method of claim 16 wherein the sugar is L-glucose.

18. The method of claim 14 wherein the pellet further comprises a compound that stops incorporation of isotope-labelled substances in the assay which will disperse in the liquid medium and prevent further incorporation of isotope in the sample.

19. The method of claim 18 wherein the radioactive isotope is $^3$H-thymidine, and thymidine is the compound that stops incorporation.

20. The method of claim 18 wherein the compound for stopping incorporation is a detergent for lysis of cell membranes.

21. The method of claim 18 wherein the compound for stopping incorporation is a metabolic inhibitor.

22. The method of claim 14 further comprising the step of compacting the sample particles and scintillant particles before using the photodetector.

23. The method of claim 22 wherein the pellet further comprises particles of a material which aids in the transmission of light from the scintillant particles to the photodetector means following compaction of the composite sample.

24. The method of claim 23 wherein the particles which aid in the transmission of light are made of a material selected from the group consisting of di-isophenyl naphthalene and tetramethylmethylbenzene, as well as combinations thereof.

25. The method of claim 14 wherein at least some of the scintillant particles are meltable and comprising the further step of heating the sample particles and scintillant particles after filtration to thereby bind the scintillant particles and sample particles together.

26. The method of claim 25 further comprising the step of compacting the sample particles and scintillant particle while heating.

27. The method of claim 14 wherein the pellet further comprises particles which are meltable and further comprising the further step of heating the meltable particles, sample particles and scintillant particles after filtration to thereby bind the scintillant particles and sample particles together.

28. The method of claim 27 further comprising the step of compacting the sample particles and scintillant particle while heating.

29. A method for filtration assaying a particulate sample labelled with low-energy radioactive isotoes measurable by scintillation counting, the method comprising the steps of:
   providing a sample comprising sample particles labelled with low-energy radioactive isotopes in a liquid medium;
   providing a pellet comprising scintillant particles held together by a binder material which releases the scintillant particles in the liquid medium;
   adding the pellet to the liquid medium;

simultaneously filtering the sample particles and scintillant particles in the liquid medium with a filter medium adapted to retain the sample particles and the particles of scintillant, such that after filtration the sample particles are each surrounded by scintillant; and using a photodetector to detect the degree of scintillation of the sample on the filter medium.

30. The method of claim 29 wherein the pellet comprises meltable particles, and further comprising the step of heating meltable particles, sample particles and scintillant particles after filtration to thereby bind the scintillant particles and sample particles together.

31. The method of claim 30 further comprising the step of compacting the sample particles and scintillant particle while heating.

* * * * *

UNITED STATES PATENT AND TRADEMARK OFFICE
CERTIFICATE OF CORRECTION

PATENT NO. : 5,268,301
DATED : December 7, 1993
INVENTOR(S) : Colin G. Potter

It is certified that error appears in the above-indentified patent and that said Letters Patent is hereby corrected as shown below:

ON THE TITLE PAGE

Under "References Cited" please add the following:

FOREIGN PATENT DOCUMENTS

|         378 059 | 07/1990 | EPO  |
| WO 90/11524     | 10/1990 | PCT  |
|        8902 088 | 03/1989 | WIPO |
|        8911 664 | 11/1989 | WIPO |

Column 5,
In claim 2, line 2, delete "filer" and substitute --filter--.

Column 6,
In claim 29, line 2, delete "isotoes" and substitute --isotopes--.

Signed and Sealed this

Twenty-eight Day of February, 1995

Attest:

BRUCE LEHMAN

Attesting Officer        Commissioner of Patents and Trademarks